United States Patent [19]

Horn et al.

[11] Patent Number: 5,302,569
[45] Date of Patent: Apr. 12, 1994

[54] COPPER/ZINC OXIDE/ALUMINUM OXIDE-CONTAINING CATALYSTS

[75] Inventors: Gerhard Horn, Oberhausen; Carl D. Frohning, Wesel, both of Fed. Rep. of Germany

[73] Assignee: Hoechst Aktiengesellschaft, Fed. Rep. of Germany

[21] Appl. No.: 931,019

[22] Filed: Aug. 17, 1992

[30] Foreign Application Priority Data

Aug. 17, 1991 [DE] Fed. Rep. of Germany ....... 4127318

[51] Int. Cl.⁵ .................. B01J 23/72; B01J 23/80; B01J 37/03; B01J 21/04
[52] U.S. Cl. .................. 502/342; 502/307; 502/324; 502/238; 502/329; 502/244; 502/245
[58] Field of Search ............ 502/342, 307, 324, 238, 502/329, 244, 245

[56] References Cited

U.S. PATENT DOCUMENTS

| | | | |
|---|---|---|---|
| 4,107,089 | 8/1978 | Bondar et al. | 502/307 |
| 4,535,071 | 8/1985 | Schneider et al. | 502/342 |
| 5,155,086 | 10/1992 | Thakur et al. | 502/342 |

FOREIGN PATENT DOCUMENTS

| | | |
|---|---|---|
| 125689 | 5/1984 | European Pat. Off. . |
| 152809 | 1/1985 | European Pat. Off. . |
| 404408 | 12/1990 | European Pat. Off. . |
| 424069 | 4/1991 | European Pat. Off. . |
| 482753 | 4/1992 | European Pat. Off. . |
| 0399097 | 9/1973 | U.S.S.R. ............... 502/342 |
| 1159035 | 7/1969 | United Kingdom . |
| 1366367 | 9/1974 | United Kingdom . |

*Primary Examiner*—Helen M. S. Sneed
*Assistant Examiner*—Douglas J. McGinty
*Attorney, Agent, or Firm*—Jordan B. Bierman

[57] ABSTRACT

An unreduced catalyst which contains, per 100 parts by weight of CuO, 40 to 130 parts by weight of ZnO, 2 to 50 parts by weight of $Al_2O_3$ and, optionally, 0.5 to 8 parts by weight of an oxide of Mn, Mo, V, Zr and/or an alkaline earth metal, and, also optionally, 2 to 80 parts by weight of a support. The catalyst has a total BET surface area of 80 to 175 m²/g, 75% to 95% of the total BET surface area is formed by pores having a radius $r_p \leq 15$ nm. The invention further relates to a process for the production of the catalyst and its use for the hydrogenation of aldehydes.

24 Claims, No Drawings

COPPER/ZINC OXIDE/ALUMINUM OXIDE-CONTAINING CATALYSTS

This Application claims the benefit of the priority of German Application P 41 27 318.4, filed Aug. 17, 1991.

The present invention relates to copper-containing catalysts having comparatively high total BET surface areas and a defined pore radius distribution, as well as to a process for the preparation thereof.

BACKGROUND OF THE INVENTION

Copper-containing catalysts, like nickel catalysts, are used to a considerable extent in industrial processes; they play a significant role, for example, in hydrogenation and dehydrogenation. In this case, the starting material to be converted is passed through the fixed catalyst either in the gaseous state (gas phase catalysis) or in the liquid state (liquid phase catalysis). The catalyst can also be used in a finely divided state as a slurry (suspension catalysis).

Catalysts which, along with copper, also contain chromium have a very broad application range. These catalysts are also known as copper chromite catalysts or Adkins catalysts. However, the use of Adkins catalysts is not without problems since chromium (VI) compounds, which are considered to be carcinogenic and require appropriate safety measures during handling, are used during their preparation. Moreover, relatively large amounts of waste water are produced in the course of the preparation, which waste water is polluted by the presence of copper, chromium (VI), and ammonium compounds. Such waste water is undesirable, since the copper and also the chromium (VI) compounds have a highly toxic effect on microorganisms and can be removed from the waste water only by a complex treatment process.

Besides copper chromite catalysts, nickel catalysts have proven suitable in many respects. However, because of their very high activity, nickel catalysts lead, in particular at relatively high reaction temperatures, to uncontrolled side reactions and secondary reactions, for example cleavages, transalkylations, and/or rearrangements. This favors the formation of undesired by-products and/or secondary products. Copper catalysts are also known which do not contain chemically bound chromium. However, these catalysts do not have the properties of either the Adkins catalysts or the nickel catalysts.

Thus, DOS 20 56 612 describes a catalyst composed of solid solutions of the series $(Cu_xZn_y)Al_2(OH)_{1.6}CO_3 \cdot 4H_2O$, where x and y can have values from 0.5 to 5.5 and the sum of x and y is 6. The solid solutions are obtained by precipitation at a pH of 4.5 to 5.5 by adding a basic precipitant, for example an aqueous $Na_2CO_3$ solution, to an aqueous solution containing copper nitrate, zinc nitrate, and aluminum nitrate. The catalyst in unreduced form containing CuO, ZnO, and $Al_2O_3$ is used in the reaction of a gas mixture composed of carbon monoxide, carbon dioxide, and hydrogen to give methanol.

EP 125,689 relates to a catalyst for methanol synthesis containing CuO, ZnO, and $Al_2O_3$ having a Cu/Zn atomic ratio between 2.8 and 3.8 (corresponding to 26.9 to 36.5 parts by weight of ZnO per 100 parts by weight of CuO) and an $Al_2O_3$ fraction of 8% to 12% by weight. $Al_2O_3$ is used as colloidal aluminum hydroxide in the preparation, and Cu and Zn are introduced into the catalyst by precipitation from metal salt solutions. 20% to 40% of the pores have a diameter of 2.0 to 7.5 nm (20 to 75 Å)—corresponding to a pore radius $r_p$ of 1.0 to 3.75 nm (10 to 37.5 Å)—and 60% to 80% of the pores, based in each case on the total number of pores, have a diameter greater than 7.5 nm (75 Å), which corresponds to a pore radius $r_p$ of more than 3.75 nm (37.5 Å). The catalysts described in more detail in the examples have, in the unreduced state, a BET surface area of 100 to 127 $m^2/g$, 32% to 42% of the pores have a diameter of 2.0 to 7.5 nm ($r_p=1.0$ to 3.75 nm), and 57% to 68% of the pores have a diameter larger than 7.5 nm ($r_p$ is greater than 3.75 nm).

As the preceding remarks demonstrate, there is a requirement for a catalyst which can be used, at least within a specific application area, in place of both Adkins catalysts and nickel catalysts. Moreover, problems in the preparation of this catalyst, such as handling carcinogenic chromium (VI) compounds, production of waste water containing pollutants, and disposal of chromium-containing used catalysts, are to be avoided. Furthermore, the novel catalyst is to ensure, in particular at relatively high temperatures, a high conversion with high activity and a high selectivity of the reaction; i.e. the undesired side reactions and secondary reactions typical of nickel catalysts are to be avoided as far as possible.

This applies, inter alia, especially to an important area of application for copper chromite or Adkins catalysts and also nickel catalysts; namely, the catalytic hydrogenation of aldehydes to the corresponding alcohols. In this area, the novel catalyst must be capable of replacing not only the nickel catalysts, but also the copper chromite or Adkins catalysts.

DESCRIPTION OF THE INVENTION

All parts referred to herein are by weight. The object is achieved by a catalyst containing, per 100 parts of CuO, 40 to 130 parts of ZnO, 2 to 50 parts of $Al_2O_3$. In its unreduced state, the catalyst has a total BET surface area of 80 to 175 $m^2/g$, and 75% to 95% of the total BET surface area is formed by pores having a radius $r_p \leq 15$ nm. Optionally, 0.5 to 8 parts of an oxide of Mn, Mo, V, Zr, alkaline earth metals, and mixtures thereof are included.

A further characteristic of the catalyst is its relatively large active copper metal surface area after reduction. In the reduced catalyst, this is 30 to 125, in particular 35 to 100, preferably 40 to 85, $m^2/g$ of Cu and thus exceeds the active copper metal surface area of corresponding copper chromite catalysts. The method of determination is to be taken from M. J. Juys, P. H. van Oeffelt, W. G. J. Brouwe, A. P. Pijpers and J. J. F. Scholten, Applied Catalysis, 46 (1989), pages 161 to 173.

The catalyst contains in its unreduced state, per 100 parts of CuO, 40 to 130, in particular 45 to 100, preferably 45 to 80, parts of ZnO, and 2 to 50, in particular 3 to 40, preferably 4 to 30, particularly preferably 4 to 11, parts of $Al_2O_3$.

If desired, the catalyst can also comprise additional substances. These include oxides of manganese, molybdenum, vanadium, zirconium, and/or alkaline earth metals. Per 100 parts of CuO; they are present in amounts of 0.5 to 8, in particular 1 to 6, preferably 2 to 4, parts calculated as MnO, $MoO_3$, $V_2O_5$, $ZrO_2$ and MeO, where Me is an alkaline earth metal. Additional substances which are particularly suitable are manganese oxide and/or an alkaline earth metal oxide. The alkaline earth metal oxide is preferably of Mg, Ca, or Ba, in particular Ca or Ba, most preferably Ba.

An important characteristic of the catalyst according to the invention is the comparatively high total BET surface area. This is 80 to 175, in particular 85 to 160, preferably 90 to 155, m²/g of catalyst as measured in the unreduced state. The total BET surface area is taken to mean the surface area determined by adsorption of nitrogen by the Brunauer, Emmett and Teller method (BET) as described in J. Amer. Chem. Soc., 60 (1938) 309.

Another important characteristic of the catalyst is the defined distribution of the pore radii, i.e. a high proportion of the total BET surface area is formed by pores having a radius $r_p \leq 15$ nm (150 Å). This proportion is 75% to 95%, in particular 80% to 92%, most preferably 84% to 90% of the total BET surface area. It is also preferable that 50% to 85%, in particular 60% to 80%, of the total BET surface area be formed by pores having a radius $r_p \leq 9$ nm (90 Å). Advantageously, 5% to 45%, in particular 15% to 40%, most desirably 18% to 30% of the total BET surface area comprises pores, of which $r_p = 9$ to 15 nm.

It should be noted that the preceding details of the total BET surface area and pore radii are, in each case, based on the catalyst in unreduced form. The determination of the pore radii is carried out by evaluation of the desorption isotherms with the aid of the Kelvin equation according to C. Pierce, J. Phys. Chem. 57, (1953) 149.

The catalyst can, if desired, contain a support in addition to the above-mentioned constituents. For best results, per 100 parts of CuO, it contains 2 to 80, in particular 4 to 60, preferably 5 to 35, parts of the support. The supports used can be conventional materials which are insoluble in water. Suitable support materials include $SiO_2$, kieselguhr, silica gel and, in particular, $Al_2O_3$.

The unreduced, calcined catalyst contains 94% to 97% by weight of CuO, ZnO, $Al_2O_3$, and the additives, which include oxides of manganese, molybdenum, vanadium, zirconium, and/or an alkaline earth metal. If desired, a support is also present. The remaining 3% to 6% by weight is composed of physically and/or chemically bound water, any hydroxyl groups still present, oxides of a composition other than that corresponding to the formula on which the calculation is based, carbonate fractions, and relatively small amounts of substances which are used in the preparation, especially precipitants.

The invention further relates to a catalyst in reduced form. The CuO is converted by the reduction into metallic Cu, whereby the catalyst is activated. In its reduced form, the catalyst contains, per 100 parts of Cu, 48 to 163, in particular 56 to 125, preferably 56 to 100, parts of ZnO; 2.4 to 63, in particular 3.7 to 50, preferably 5.0 to 37.5, particularly preferably 5 to 13.8, parts of $Al_2O_3$; and, optionally, 0.6 to 10, in particular 1.2 to 7.5, preferably 2.4 to 5.0, parts of an oxide of Mn, Mo, V, Zr and/or an alkaline earth metal.

Catalysts are particularly suitable which also contain Mn or Ba oxides along with Cu, ZnO, and $Al_2O_3$. The catalyst can additionally contain a support material. A catalyst of this type preferably includes, per 100 parts of Cu, 2.4 to 100, in particular 4.8 to 75, preferably 6 to 44, parts of the support. The support materials include substances which are insoluble in water, in particular $SiO_2$, such as kieselguhr or silica gel, and/or $Al_2O_3$, preferably $Al_2O_3$.

The remaining parameters, namely the total BET surface area and the pore radius distribution, roughly correspond to those described for the unreduced catalyst.

The process for the preparation of the catalyst according to the invention starts with an aqueous solution containing salts of copper, zinc, aluminum and optionally Mn, Mo, V, Zr, and/or an alkaline earth metal. This solution (also termed mixed salt solution) contains 10 to 100, in particular 20 to 80, preferably 30 to 60, grams of Cu/liter, 10 to 50, in particular 15 to 40, preferably 10 to 30, grams of Zn/liter; and Al corresponding to 2 to 80, in particular 5 to 60, preferably 10 to 40, grams of $Al_2O_3$/liter. The mixed salt solution also may contain 3 to 80, in particular 5 to 50, preferably 10 to 30, grams of Mn, Mo, V, Zr and/or an alkaline earth metal, calculated as MnO, $MoO_3$, $V_2O_5$, $ZrO_2$ and MeO, respectively, wherein Me is an alkaline earth metal.

The mixed salt solution is prepared by dissolving water-soluble inorganic, organic, or complex salts of the above-mentioned elements in water. Highly suitable salts are the sulfates, chlorides, acetates, propionates, butyrates, and nitrates. It has proved particularly expedient to use sulfates, chlorides, acetates, and nitrates, especially the nitrates, in the preparation of the mixed salt solution.

In order to prevent a partial, undesired hydrolysis and to influence the precipitation favorably, it is recommended to maintain an excess of free acid in the mixed salt solution. The mixed salt solution, if necessary by addition of acid, is expediently adjusted to a pH below 4.5, in particular to a pH between 2.0 and 4.0. The acids used can be mineral acids such as pH hydrochloric acid, sulfuric acid, and nitric acid, nitric acid being particularly suitable. By this means it is ensured that the precipitation proceeds under reproducible conditions, and, moreover, that a precipitation product as uniform as possible is obtained.

The mixed salt solution and the aqueous solution of a basic precipitant are separately, but simultaneously, brought together with mixing. If a support is desired, it is present when the solutions are mixed together.

The precipitant is an aqueous solution of a basic compound, in particular an aqueous solution of an alkali metal carbonate, alkali metal hydrogen carbonate, alkali metal hydroxide, ammonium hydroxide, or ammonium carbonate. Mixtures thereof can also be used. An aqueous solution containing $Na_2CO_3$ and/or $NaHCO_3$ is particularly suitable. The precipitant should have a pH of 7.5 to 13, in particular 8 to 12, preferably 9 to 11.

The aqueous precipitant solution contains 0.1 to 4.0, in particular 0.6 to 3.0, preferably 1.6 to 2.4, chemical equivalents of basic compound/liter of solution. Very good results are obtained with aqueous solutions which contain 0.3 to 1.5, in particular 0.8 to 1.2, mols of alkali metal carbonate/liter of solution.

To ensure as complete a precipitation as possible and at the same time to obtain a particularly homogeneous coprecipitate composed of the corresponding basic compounds of copper, zinc, aluminum, and, the optional additives (if present), the basic compound is used in excess. The stoichiometric excess is generally 5% to 60%, in particular 10% to 50% of the basic compound. The use of a 15% to 30% excess of basic compound has proved to be particularly expedient. The excess is based on, in each case, to the amount of basic compound which is required for complete precipitation of the metals contained in the mixed salt solution.

The stoichiometric excess should be such that, on the one hand, the precipitation of as homogeneous a coprecipitate as possible is indeed assured and, on the other hand, a precipitation of the metal ions contained in the mixed salt solution occurs to the desired extent in each case, preference being given to the most complete precipitation possible.

The precipitation is caused by bringing together the mixed salt solution and the precipitant separately, but simultaneously, either continuously or discontinuously but with intensive mixing. The precipitation of the coprecipitate composed of the basic compounds is brought about by bringing together the mixed salt solution and the precipitant comparatively slowly. The precipitation time should be at least 10, in particular at least 15, preferably at least 20, minutes. The mixed salt solution and the solution of the basic precipitant are advantageously heated to a predetermined temperature which roughly corresponds to the temperature at which the precipitation is carried out.

It has generally proved to be expedient to keep to a precipitation time of 10 to 100, in particular 15 to 95, preferably 20 to 90, minutes. The precipitation time can be altered by selection of an appropriate addition rate of mixed salt solution and precipitant, in particular in the case of discontinuous precipitation. However, in the case of the continuous method, in addition to the addition rates of the mixed salt solution and precipitant, the throughput relative to the reaction volume is also to be considered.

During the precipitation, a constant pH is employed within a pH range of 6.5 to 8.5, in particular 7.6 to 8.0. Variations of the pH should be kept as small as possible to ensure the preparation of a particularly homogeneous coprecipitate. The variations in pH should be limited to $-0.5$ to $+0.5$, preferably $-0.2$ to $+0.2$.

The precipitation is carried out at temperatures above 70° C., in particular in a range of 75° C. to 95° C., preferably 75° C. to 85° C. For this purpose, it is sufficient to raise the temperature of the substances participating in the precipitation, namely the mixed salt solution and the precipitant, to an appropriately high level. During the precipitation, it is advisable to hold the temperature as constant as possible. The deviations from the predetermined temperature should not exceed $\pm 2°$ C., in particular $\pm 1°$ C. Larger variations in the precipitation temperature can influence the quality, for example particle size, homogeneity, and structure of the coprecipitate in a disadvantageous manner.

Subsequent to the precipitation, the coprecipitate, optionally after brief further stirring, is separated off from the mother liquor, for example by decanting and/or filtering, and is carefully washed. The amount of wash water used, the flow rate and temperature of the wash water as well as the duration of the washing process influence the elimination of undesired constituents from the coprecipitate, in particular the dissolving out of nitrate ions and alkali metal ions. Increasing amounts of wash water, high temperatures of the wash water, and long duration of the wash process promote a particularly extensive dissolving out, whereas relatively low amounts of wash water, low temperatures of the wash water and short duration of the wash process lead to reduced dissolving out.

It is generally sufficient to maintain a temperature of 55° C. to 85° C., in particular 60° C. to 75° C. during the washing. Higher wash temperatures can have disadvantageous effects on the quality of the precipitate. The use of temperatures which are too low can lead to undesired constituents not being eliminated to the required extent from the coprecipitate. This can also have an unfavorable effect on the quality of the useful product.

Generally, 5 to 50, in particular 10 to 30, preferably 15 to 25, liters of wash water are used per kg of coprecipitate. The duration of the wash process should be of sufficient length; it desirably is at least 60, in particular at least 70, preferably at least 80, minutes. A sufficient washing duration is generally 80 to 140, in particular 85 to 130, preferably 90 to 120, minutes.

The wash process can be carried out in a single step or in a plurality of successive stages, by appropriately apportioning the total amount of wash water required. Which procedure is preferred depends on the individual case. In general, both a single stage and a multistage process lead to the desired result. A multistage wash process can be advantageous in many cases, since less wash water is usually required than in a single stage process.

Monitoring of the wash process is facilitated by determination of the compounds, such as $NaNO_3$, which have been dissolved out by monitoring the amounts present in the wash water. Monitoring in this manner can be dispensed with if the washing process is performed under standardized and controlled conditions, for example with a preset amount of wash water, temperature, and duration. If required, the washed material can be converted into a particulate form. Proven processes, such as, for example, extrusion, can be used for shaping.

Drying is carried out in stages at elevated temperatures, preferably at increasing temperatures. It has proved sufficient to carry out the drying at temperatures of 50° C. to 120° C., in particular 55° C. to 100° C., preferably 60° C. to 90° C. with the use of conventional processes, such as disposing the material to be dried in a fixed or moving bed, e.g. in a fluidized layer. Drying is carried out until a residual water content of about 2% to 15%, in particular 3% to 10% by weight of water, based on the dried coprecipitate, is attained.

The subsequent calcination is carried out at 250° C. to 450° C., in particular 320° C. to 400° C. over a period of 3 to 10, in particular 4 to 8, hours. The calcined catalyst can be used either directly in powder form for suspension hydrogenations or after shaping, such as tableting or pelleting, as a fixed-bed catalyst.

The calcined catalyst is reduced (activated) to prepare the actual catalyst active in hydrogenation. For this purpose, the calcined, unreduced catalyst is treated at 130° C. to 190° C., optionally at elevated pressure, with hydrogen. It has proved particularly expedient to carry out the reduction with a hydrogen/nitrogen mixture containing 1 to 5% by volume of hydrogen. As a result of the treatment with hydrogen, metallic Cu is formed from CuO.

The catalyst according to the invention can be used advantageously for hydrogenation of aldehydes, such as aromatic and aliphatic straight and/or branched chain aldehydes, in the liquid phase and also in the gaseous phase. An advantage is that high conversions and good selectivities are achieved even at comparatively high temperatures, without formation of undesired byproducts to any significant extent. In this manner, aldehydes and aldehyde derivatives of low reactivity, for example unsaturated aliphatic aldehydes, can be hydrogenated to give the corresponding alcohols without difficulty.

The examples below illustrate the present invention without restricting it.

EXAMPLE 1

Preparation of a catalyst containing CuO, ZnO and $Al_2O_3$ 4,356 g of $Cu(NO_3)_2.3H_2O$, 2,615 g of $Zn(NO_3)_2.6H_2O$, and 895.8 g of $Al(NO_3)_3.9H_2O$ are dissolved in 18 liters of deionized water to form a mixed salt solution which is heated to 80° C. The solution of the basic precipitant is obtained by dissolving 3,750 g of $Na_2CO_3$ in 30 liters of deionized water. This solution is also heated to 80° C.

8 liters of deionized water are placed in a precipitation vessel which is equipped with a stirrer and are heated to 80° C. with stirring. The mixed salt solution and the solution of the basic precipitant are introduced into the precipitation vessel separately, but simultaneously, in the course of 20 minutes with vigorous stirring. The flow rates of the two solutions are matched to each other so that a pH of 7.5 to 7.8 is maintained in the precipitation vessel. The temperature in the precipitation vessel is held constant at 80° C.

After completion of the precipitation, the suspension present in the precipitation vessel is stirred for a further 2 minutes. The precipitate (coprecipitate) is separated off from the mother liquor by filtration and is then washed for a period of 2 hours with 120 liters of water at a temperature of 60° C. to 65° C. The washed filtercake is dried either in extruded form or by spray drying to a final moisture content of $\leq 5\%$ by weight, based on the catalyst mass.

The dried precipitation product is calcined for 4 hours in a stream of $N_2$ at 380° C. The calcined catalyst contains 47.5% by weight of Cu. It contains, per 100 parts of CuO, 49.5 parts of ZnO, 8.4 parts of $Al_2O_3$, 3.7 parts of $CO_2$ and 0.12 parts of $Na_2O$.

The total BET surface area of the catalyst is 128 $m^2/g$. 85% of the total BET surface area is formed by pores having a radius $r_p \geq 15$ nm. The copper metal surface area of the reduced catalyst is 68 $m^2/g$ of Cu.

EXAMPLE 2

Preparation of a catalyst containing CuO, ZnO, $Al_2O_3$ and BaO 4,356 g of $Cu(NO_3)_2.3H_2O$, 2,615 g of $Zn(NO_3)_2.6H_2O$, 895.8 g of $Al(NO_3)_3.9H_2O$, and 73.2 g of $Ba(NO_3)_2$ are dissolved in 18 liters of deionized water to form the mixed salt solution which is heated to 80° C. The solution of the basic precipitant is obtained by dissolving 3,750 g of $Na_2CO_3$ in 30 liters of deionized water. This solution is also heated to 80° C. The same procedure as set forth in Example 1 is thereafter followed.

The calcined catalyst contains 46.5% by weight of Cu. It contains, per 100 parts of CuO, 49.8 parts of ZnO, 8.2 parts of $Al_2O_3$, 3.6 parts of $CO_2$, 0.12 parts of $Na_2O$, and 2.0 parts of BaO. The total BET surface area of the unreduced catalyst is 127 $m^2/g$. 88% of the total BET surface area is formed by pores having a radius $r_p \leq 15$ nm. The copper metal surface area of the reduced catalyst is 65 $m^2/g$ of Cu.

EXAMPLE 3

Preparation of a catalyst containing CuO, ZnO, $Al_2O_3$ and MnO 1,936 g of $Cu(NO_3)_2.3H_2O$, 1,152.4 g of $Zn(NO_3)_2.6H_2O$, 234.2 g of $Al(NO_3)_3.9H_2O$, and 78.9 g of $Mn(NO_3)_2.4H_2O$ are dissolved in 10.2 liters of deionized water to form a mixed salt solution which is heated to 80° C. The solution of the basic precipitant is obtained by dissolving 1,620 g of $Na_2CO_3$ in 15.4 liters of deionized water. This solution is also heated to 80° C.

6 liters of deionized water are placed in a precipitation vessel which is equipped with a stirrer and are heated to 80° C. with stirring. The mixed salt solution and the solution of the basic precipitant are introduced into the precipitation vessel separately, but simultaneously, over a period of 17 minutes with vigorous stirring.

Thereafter, the procedure of Example 1 is followed. The calcined catalyst contains 47.3% by weight of Cu. It contains, per 100 parts of CuO, 53.3 parts of ZnO, 5.3 parts of $Al_2O_3$, 2.9 parts of MnO, 3.2 parts of $CO_2$ and 0.15 parts of $Na_2O$.

The total BET surface area of the unreduced catalyst is 95 $m^2/g$. 85% of the total BET surface area is formed by pores of a radius $r_p \leq 15$ nm. The copper metal surface area of the reduced catalyst is 54 $m^2/g$ of Cu.

EXAMPLE 4

Preparation of a catalyst containing CuO, ZnO, $Al_2O_3$, MnO and support 1,459 g of $Cu(NO_3)_2.3H_2O$, 700.7 g of $Zn(NO_3)_2.6H_2O$, 176.5 g of $Al(NO_3)_3.9H_2O$, and 59.4 g of $Mn(NO_3)_2.4H_2O$ are dissolved in 7.7 liters of deionized water to form a mixed salt solution which is heated to 85° C. The solution of the basic precipitant is obtained by dissolving 1,505 g of $Na_2CO_3$ in 14.2 liters of deionized water. This solution is also heated to 85° C.

48 g of finely divided $Al_2O_3$ (commercial product "Type H" from Martinswerk/Bergheim), as a support, and 4 liters of deionized water are placed in a precipitation vessel which is equipped with a stirrer, and the mixture is heated to 85° C. with stirring. The mixed salt solution and the solution of the basic precipitant are introduced into the precipitation vessel separately, but simultaneously, over a period of 24 minutes with vigorous stirring. The flow rates of the two solutions are matched to each other so that a pH of 7.7 to 8.0 is maintained in the precipitation vessel. The temperature in the precipitation vessel is held constant at 85° C. After the precipitation is completed, the procedure as given in Example 1 is followed, except that the dried precipitation product containing the support is calcined for 5 hours in the $N_2$ stream at 380° C.

The calcined catalyst contains 45.6% by weight of Cu. It contains, per 100 parts of CuO, 43.2 parts of ZnO, 13.3 parts of $Al_2O_3$, 2.8 parts of MnO, 3.7 parts of $CO_2$, and 0.1 parts of $Na_2O$. The total BET surface area of the unreduced catalyst is 117 $m^2/g$. 83% of the total BET surface area is formed by pores having a radius $r_p \leq 15$ nm. The copper metal surface area of the reduced catalyst is 76 $m^2/g$ of Cu.

EXAMPLE 5

Hydrogenation of n-butanal 3 liters of the catalyst prepared according to Example 1 are placed in pelleted form (6×5 mm pellets) in a jacketed tube reactor having an internal diameter of 38 mm.

The catalyst-containing layer is heated to 160° C. and, for activation, an $N_2$ stream containing 3% by volume of $H_2$ is passed through the catalyst layer at normal pressure at a space velocity (V/Vh) of 1,000 liters of the N₂ stream/liter of catalyst per hour. The feed of the N₂ stream containing 3% by volume of H₂ is terminated after 24 hours and the temperature in the catalyst layer is reduced to 143° C.

n-Butanal is evaporated in an evaporator at 130° C., with feeding of a H₂ gas stream (98% hydrogen) which is adjusted to a pressure of 0.35 MPa and a flow rate of 10.2 Nm³/h. The resulting gas mixture is heated to 143° C. and is fed to the solid catalyst in the jacketed tube reactor.

Over a period of 8 hours each, 600, 1,200, and 1,800 ml of liquid n-butanal/h are initially used, corresponding to a space velocity of 0.2, 0.4 and 0.6, respectively. An hourly quantity of 3,000 ml of liquid n-butanal (V/Vh=1) is then fed to the reactor in evaporated form.

The reaction product produced has the composition, determined by gas chromatographic analysis, of

| n-Butanal | 0.1 to 0.3% by weight |
| n-Butanol | 99.5 to 99.7% by weight |
| i-Butanol | 0.04% by weight |
| Remainder byproducts. | |

The CO number is 1.0 [mg of KOH/g].

EXAMPLE 6

Hydrogenation of 2-ethylhexenal 3 liters of the catalyst of Example 4 are placed in tableted form (6×5 mm tablets) in a jacketed tube reactor having an internal diameter of 38 mm. The catalyst is activated as described in Example 5 and the temperature in the catalyst layer is then reduced to 143° C. 1,500 ml of 2-ethylhexenal/hour (corresponding to V/Vh=0.5) are evaporated in an evaporator at 100° C. with feed of a H₂ stream (98% hydrogen) which is adjusted to a pressure of 0.15 MPa and a flow rate of 4.4 Nm³/h. The resulting gas mixture is heated to 140° C. and is fed to the solid catalyst in the jacketed tube reactor. The reaction is carried out for 2,160 hours without interruption, without any marked impairment of the course of reaction being observed.

The composition of the starting material and of the reaction product (determined by gas chromatographic analysis) are compiled in the following Table.

TABLE

| | Starting material (% by weight) | | Reaction product (% by weight) |
|---|---|---|---|
| C₃-C₇-hydrocarbon | 0.1% | | 0.3–0.4 |
| n-butanal | 1.6% | | — |
| n/i-butanol | 0.7% | | 2.2 |
| 2-ethylhexanal | 0.6 | | 0.4 |
| 2-ethylhexenal | 91.0 | | <0.01 |
| 2-ethylhexanol | 4.0 | | 96.5 |
| heavy ends | approx. 1.5 | approx. | 0.5 |

What we claim is:

1. A catalyst containing, per 100 parts by weight of CuO, 40 to 130 parts by weight of ZnO, and 2 to 50 parts by weight of Al₂O₃, said catalyst having a total BET surface area of 80 to 175 m²/g, 75% to 95% of said total BET surface area consisting of pores having a radius $r_p \leq 15$ mn.

2. The catalyst of claim 1 which contains, per 100 parts by weight of CuO, 0.5 to 8 parts by weight of an oxide of a metal selected from the group consisting of Mn, Mo, V, Zr, alkaline earth metals, and mixtures thereof.

3. The catalyst of claim 1 wherein said CuO has an active copper metal surface area of 30 to 125 m²/g of copper.

4. The catalyst of claim 3 wherein said copper surface area is 40 to 85 m²/g of copper.

5. The catalyst of claim 1 which contains, per 100 parts by weight of CuO, 45 to 100 parts by weight of ZnO and 3 to 40 parts by weight of Al₂O₃.

6. The catalyst of claim 1 which contains, per 100 parts by weight of CuO, 45 to 80 parts by weight of ZnO and 4 to 11 parts by weight of Al₂O₃.

7. The catalyst of claim 2 wherein said metals are selected from the group consisting of Mn, alkaline earths, or mixtures thereof.

8. The catalyst of claim 1 wherein said total BET surface area is 85 to 160 m²/g.

9. The catalyst of claim 8 wherein said total BET surface area is 90 to 155 m²/g.

10. The catalyst of claim 1 wherein 80% to 92% of said total BET surface area is comprised of pores having a radius $r_p \leq 15$ nm.

11. The catalyst of claim 10 wherein 84% to 90% of said total BET surface area is comprised of pores having a radius $r_p \leq 15$ nm.

12. The catalyst of claim 1 wherein 50% to 85% of said total BET surface area is comprised of pores having a radius $r_p \leq 9$ nm.

13. The catalyst of claim 12 wherein 60% to 80% of said total BET surface area is comprised of pores having a radius $r_p \leq 9$ nm.

14. The catalyst of claim 1 wherein 5% to 45% of said total BET surface area is comprised of pores having a radius $r_p = 9$ to 15 nm.

15. The catalyst of claim 14 wherein 18% to 30% of said total BET surface area is comprised of pores having a radius of $r_p = 9$ to 15 nm.

16. The catalyst of claim 1 which contains, per 100 parts by weight of CuO, 2 to 80 parts by weight of a support which is insoluble in water.

17. The catalyst of claim 16 wherein said support is present in an amount of 5 to 35 parts by weight per 100 parts of said CuO.

18. The catalyst of claim 16 wherein said support is selected from the consisting of SiO₂, Al₂O₃, and mixtures thereof.

19. The catalyst of claim 18 wherein said support is selected from the group consisting of kieselguhr, silica and mixtures thereof.

20. The catalyst of claim 17 wherein said support is Al₂O₃.

21. A process for the preparation of the catalyst of claim 1 wherein a first aqueous solution, containing salts of copper, zinc, and aluminium, and a separate second aqueous solution of a basic precipitant are simultaneously, brought together and precipitated at a pH within a range of 7.6 to 8.0 and at a precipitation temperature above 70° C. to form a coprecipitate, said coprecipitate is separated off, washed with water, dried, and calcined.

22. The process of claim 21 wherein said first solution comprises salts of a metal selected from the group consisting of manganese, molybdenum, vanadium, zirconium, alkaline earths, and mixtures thereof.

23. The process of claim 21 wherein said coprecipitate is reduced after calcining.

24. The process of claim 23 wherein the coprecipitate after calcining is reduced at 130° C. to 190° C. with a hydrogen/nitrogen mixture, which contains 1.0% to 5% by volume of hydrogen.

* * * * *